United States Patent [19]

Ohkaka et al.

[11] Patent Number: 4,807,622
[45] Date of Patent: Feb. 28, 1989

[54] TUBE CUTTING AND SEPARATING IMPLEMENT FOR CONDUIT OF BLOOD OR THE LIKE

[75] Inventors: Ichizo Ohkaka, Yokohama; Hiroaki Nakajima, Tokyo, both of Japan

[73] Assignee: Kato Hatsujo Kaisha, Ltd., Yokohama, Japan

[21] Appl. No.: 909,313

[22] Filed: Sep. 19, 1986

[30] Foreign Application Priority Data

Sep. 20, 1985 [JP] Japan ................................. 60-208501
Jul. 4, 1986 [JP] Japan ................................. 61-157485

[51] Int. Cl.⁴ ............................................. A61B 17/08
[52] U.S. Cl. ..................................... 128/305; 128/326; 128/346; 30/124
[58] Field of Search ................ 128/305, 318–320, 128/325, 326, 346; 604/29, 34, 250, 905; 30/124, 131, 134, 135, 136; 251/9, 10

[56] References Cited

U.S. PATENT DOCUMENTS

| | | | |
|---|---|---|---|
| 3,106,919 | 10/1963 | Churchville | 128/346 |
| 3,323,208 | 6/1967 | Hurley, Jr. | 30/134 |
| 3,631,858 | 1/1972 | Ersek | 128/318 |
| 3,786,816 | 1/1974 | Wolvek | 128/325 |
| 3,942,228 | 3/1976 | Buckman et al. | 251/10 |
| 4,097,020 | 6/1978 | Sussman | 251/10 |
| 4,602,629 | 7/1986 | Schnirman | 128/346 |

Primary Examiner—C. Fred Rosenbaum
Assistant Examiner—Mario Costantino
Attorney, Agent, or Firm—Foley & Lardner, Schwartz, Jeffery, Schwaab, Mack, Blumenthal & Evans

[57] ABSTRACT

A tube cutting and separating implement for a conduit comprising a grasping body formed to insert the conduit therethrough and having a first section separable from a separating portion and a second section. The first and second sections respectively have first and second flow stopping portions for grasping the conduit to stop the flow and first and second holding portions for holding the flow stopping state. A cutter is disposed at the first or second section at a position displaced from the flow stopping portions for cutting the conduit. Thus, the implement can stop flow at two positions of the conduit by a simple operation and cut the conduit and separate the implement into two sections so as to allow a patient to simply and rapidly be released without loss of blood in case of an emergency.

12 Claims, 7 Drawing Sheets

TUBE CUTTING AND SEPARATING IMPLEMENT FOR CONDUIT OF BLOOD OR THE LIKE

BACKGROUND OF THE INVENTION

This invention relates to a tube cutting and separating implement for a conduit of blood or the like, attached to a tube for conducting the blood, flow of or various types of chemical solutions or gases. The implement is for cutting and separating the tube by a manual operation without losing blood when a defect occurs so that a patient dialysing in a hospital can, for example, release himself. The device also permits isolation of a dangerous medicine can be carried out rapidly.

Figure 10:
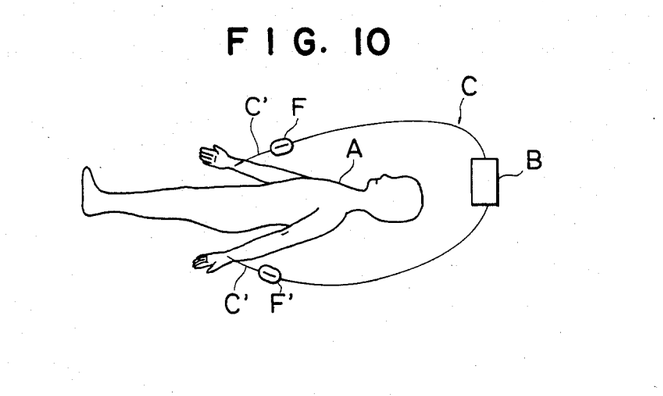
FIG. 10 is an explanatory view of the implement used for artificial dialysis.

A renal patient must be treated by artificial dialysis for 5 to 8 hours once every three days so as to purify one's blood against toxicity as is well known. As shown in FIG. 10, a blood circuit is closed by coupling the patient's body A with an artificial kidney B through a tube C used as a conduit for the blood. In this case, the coupling ends C', C' of the tube C are connected to the patient's arms so as not to be removed. Thus, the patient must remain on a bed and cannot freely move.

Figure 11:
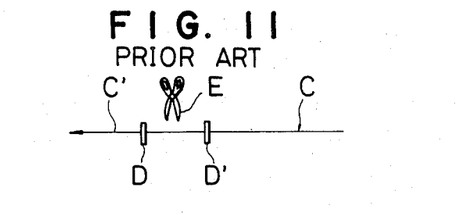
FIG. 11 is an explanatory view of conventional tube cutting means for a conduit.

Therefore, if a disaster such as an earthquake or a fire tkes place, the patient cannot escape. Thus, as shown in FIG. 11, the tube C is held using a nurse by clips D, D' to thereby stop blood flow, and cut between the clips D and D' by a pair of scissors E, and the patient may escape while attached to the coupling ends C', C'.

SUMMARY OF THE INVENTION

Accordingly, an object of this invention is to provide a tube cutting and separating implement for a conduit of blood or the like which can eliminate the abovementioned drawbacks and can stop blood flow at two positions of a tube by a simple operation and cut the tube between the two positions while the blood is stopped. The cutting and separating implements are separated into two sections so as to allow the patient to simply and rapidly release himself without losing blood such as shown in FIG. 10. Cutting and separating implements F, F' of suitable construction are attached to stop the blood flow at two positions merely by a simple operation of grasping implements F, F' which are separated to allow the patient to simply and rapidly escape without losing the blood. The implement can also be used to seal and sever various medical and industrial conduits.

In order to achieve the above and other objects, there is provided according to this invention a tube cutting and separating implement for a conduit of blood or the like comprising a grasping body formed to insert a tube or conduit therethrough and having a first section separable from a second section. The first and second sections respectively have first and second flow stopping portions for grasping the tube to stop the flow by pressing the body, and a cutter disposed in the first or second section at a position displaced from the flow stopping portons for cutting the tube by pressing the body. The flow stopping state is held by the first and second holding portions and the cutter cuts the tube between the first and second flow stopping portions.

Further, the first and second sections can be separated by a simple operation such as by bending the separate portions, cutting by the cutter or removing. Thus, in case of emergency a patient during an artificial dialysis can escape while the coupling ends C', C' of the tube C remain attached.

The above and other related objects and features of the invention will be apparent from a reading of the following description of the disclosure found in the accompanying drawings and the novelty thereof pointed out in the appended claims.

DESCRIPTION OF THE PREFERRED EMBODIMENTS

This invention will be described in detail with respect to embodiments shown in FIGS. 1 to 3. A grasping body 1 formed by an elastic transformably synthetic resin or the like has a first section 2 on the left side and a second section 3 on the right side. In the first and second embodiments in FIGS. 1 and 2, the sections 2 and 3 are integral, and in the third embodiment in FIG. 3, the sections 2 and 3 are separately formed.

Figure 2:
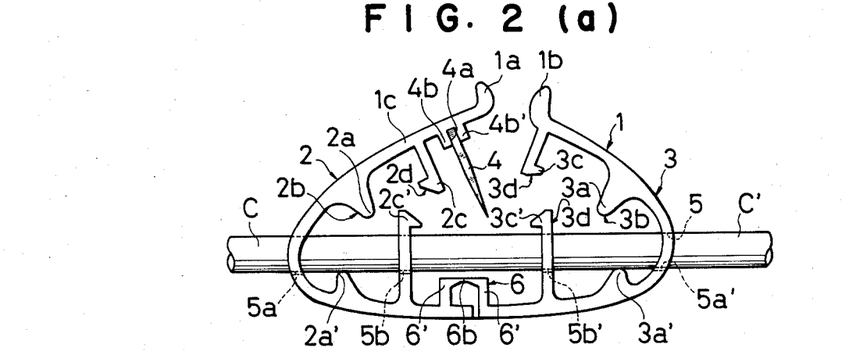
FIG. 2(a) is similar to FIG. 1(a) but shows a second embodiment according to this invention.
FIG. 2(b) is similar to FIG. 1(b) shows the second embodiment.
FIG. 2(c) is similar to FIG. 1(c) but shows the second embodiment.

The body 1 in FIG. 2 has a transformable outer peripheral frame 1c formed annularly so that ends 1a and 1b are opposed, and the first and second sections 2 and 3 have first and second flow stopping portions 2b and 3b formed of first and econd upper projections 2a and 3a disposed at the upper position of frame 1c and slightly displaced leftward and rightward and projected toward first and second lower projections 2a' and 3a'. Adjacent to the first and second projections 2a and 3a, are the first and second holding portions 2d and 3d formed with the first and second upper pawl pieces 2c and 3c adjacent to first and second lower pawl pieces 2c' and 3c' to be engaged wit one another by manual operation as will be described in detail.

In the exemplified embodiment, at the first section 2, a cutter 4 is downwardly projected from the frame 1c. Reference numeral 4a designates the engaging groove of the cutter 4 formed by projecting strips 4b, 4b' from the frame 1c, and the cutter 4 is provided at a position displaced from the fist flow stopping portion 2b of the first section 2.

A numeral 5 designates a hole for inserting a tube C for a conduit formed by rubber or the like. In the first and second embodiments in FIGS. 1 and 2, the hole 5 is formed of first and second outer holes 5a, 5a' formed in the lower left and right sides of the frame 1c and first and second inner holes 5b, 5b' formed in the first and second lower pawl pieces 2c' and 3c'.

Figure 1A:
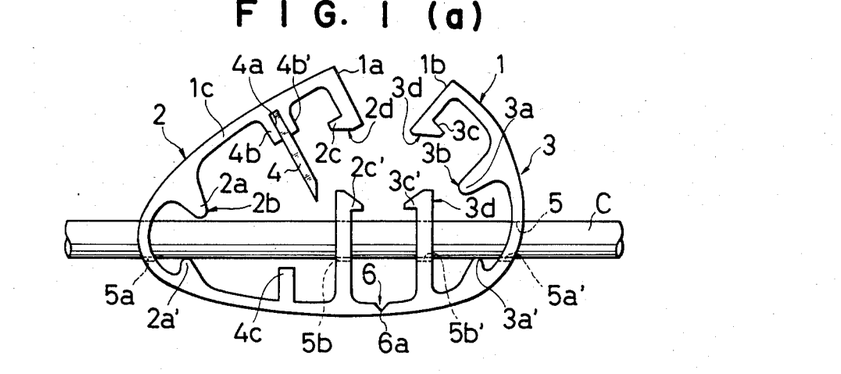
FIG. 1(a) is a front view of a first embodiment of a tube cutting and separating implement for a conduit of blood or the like before manual operation according to this invention.

In the first embodiment in FIG. 1, at the first section 2, the cutter 4 is projected downward between the right end side of the first flow stopping portion 2b and the first holding portion 2d, while in the second embodiment in FIG. 2, the cutter 4 is formed at the rightmost. Numeral 4c in FIG. 1 designates a tube bearing strip projected upward from the frame 1c so as to readily cut the tube C by the cutter 4 as will be described in detail.

Further, in the invention, the body 1 is formed with a separating portion 6 for readily separating the first section 2 from the second section 3.

The separating portion 6 in FIG. 1 is formed of a thin film 6a for breakage obtained by forming a scribing line from the inside of the frame 1c between the first lower pawl piece 2c' and the second lower pawl piece 3c' to be readily bent by one hand operation.

The separating portion 6 in FIG. 2 is formed of a thin film 6b for breakage formed at the frame 1c at the position directly under the cutter 4. The separating portion 6 is cut by the cutter 4 by applying a grasping force by manual operation of the body 1, and cutting the tube c by the cutter 4, thereby separating the sections 2 and 3. In this embodiment, the portion 6 is between rising legs 6' and 6' projected from the lower center of the frame 1c.

Figure 3A:
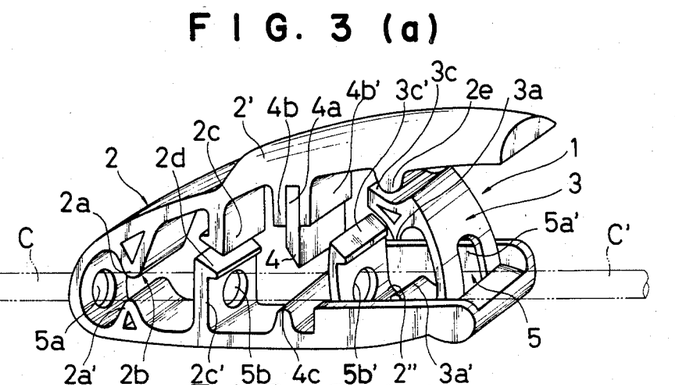
FIG. 3(a) is similar to FIG. 1(a) but shows a third embodiment according to this invention.

In the third embodiment in FIG. 3, the second section 3 has a separate second flow stopping portion 3b and a second holding portion 3d, which are contained detachably in a recess 2" formed at the lower right end of the U-shaped outer peripheral housing 2'.

Therefore, the separating portion in this third embodiment is not formed in a thin film, but is formed of separate second and first sections 3 and 2 in a contacting structure.

In FIG. 3, numeral 2e designates a pressing strip for pressing the second upper pawl piece 3c to be engaged with the second lower pawl piece 3c' of the second section 3 of separate member. In this third embodiment, the second inner hole 5b' and the second outer hole 5a' are formed in the separate second section 3, at the second lower pawl piece 3c' and the second upper pawl piece 3c.

In using the cutting and separating implement of these first to third embodiments, the tube C is inserted into the hole 5 of the first and second outer holes 5a, 5a' then first and second inner holes 5b, 5b' to a suitable position, i.e., in the case of an artificial dialysis, as shown in FIG. 10.

Figure 1B:
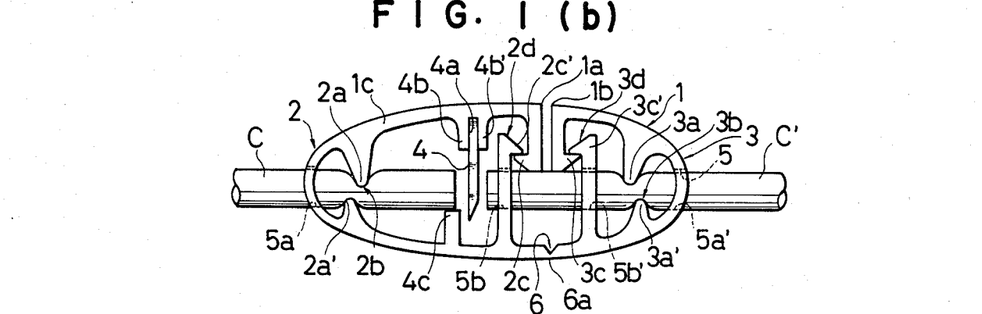
FIG. 1(b) is a front view of the first embodiment immediately after manual operation.
Figure 3B:
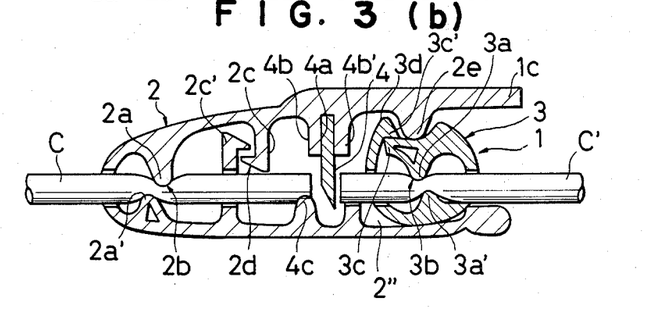
FIG. 3(b) is similar to FIG. 1(b) but shows the third embodiment.

If an emergency such as an earthquake or a fire takes place, the patient grasps by right and left hands the frame 1c of the body 1 in FIGS. 1 and 2 and the outer housing 2' of the first section 2 in FIG. 3 to collapse it. Thus, as shwon in FIGS. 1(b) to 3(b), the first and second upper projections 2a, 2b and the first and second lower projections 2a', 3a' approach to allow the first and second flow stopping portions 2b and 3b to collapse the tube c to stop the flow. At this time, the first and second upper pawl pieces 2c, 3c and the first and second lower pawl pieces 2c', 3c' are engaged to hold the flow stopping state, and the cutter 4 cuts the tube C.

Figure 1C:
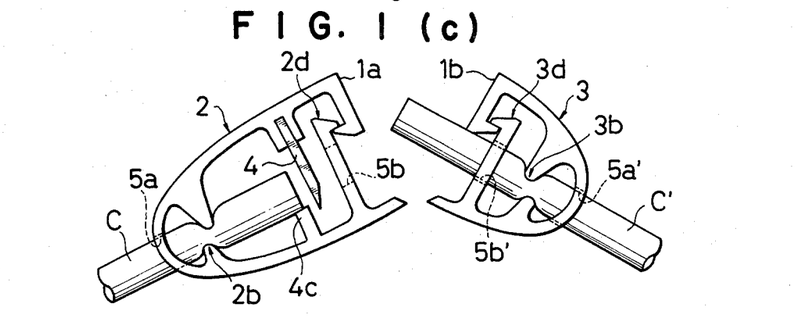
FIG. 1(c) is a front view of the first embodiment in a separated state.

Then, a patient who is treated by an artificial dialysis, as in the case of FIG. 1, further bends the frame 1c to damage the thin film 6a for breakage, thereby separating the first section 2 and the second section 3 as shown in FIG. 1(c). Thus, the patient can be released from tube C with the coupling end C' and the separated second section 3 attached.

In case of FIG. 2, the patient does not need to bend the frame as described above, but can cut the thin film 6b for breakage by the cutter 4 merely by a grasping operation. Thus the first and second sections 2, 3 can be more rapidly separated.

Figure 3C:
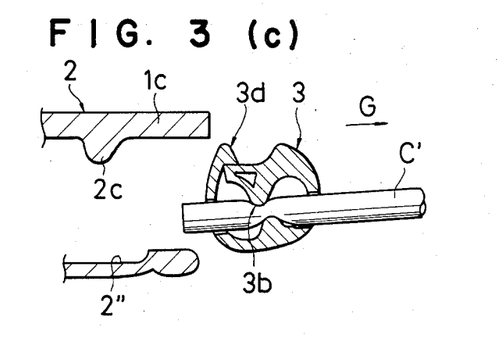
FIG. 3(c) is similar to FIG. 1(c) but shows the third embodiment.

Further, in the third embodiment in FIG. 3, after the above grasp operation, the grasping is then released, the and patient then pulls the coupling end c' in the direction of an arrow G in FIG. 3(c). Thus, the separate second section 3 is drawn from the first section 2, thereby rapidly separating both sections 2 and 3.

The, fourth to seventh embodiments in FIGS. 4 to 7 according to this invention will be further described. In the case of the fourth embodiment in FIG. 4, the second section 3 is separated from the first section 2 and disposed in a U-shaped outer peripheral housing 2' of the first section 2, at the lower right side in the same manner as the third embodiment in FIG. 3, but is different in that the second secton 3 is a bent elastic plate substantially in a C shape and capable of being annularly closed by an inherent elastic force.

More particularly, the second section 3 is normally constructed so that the second flow stopping portion 3b is formed of a second upper projection 3a forced apart from a second lower projection 3a' which contact one another due to the inherent elastic recovery force.

A second difference resides in the separating portion. In the third embodiment in FIG. 3, the second section 3 is detachably contacted with the recess 2' of the first section 3. In the fourth embodiment, the second upper projection 3a and the second lower projection 3a' are separated against the elastic force are detachably engages with the upper end 7a and the lower end 7b of the separating projection 7 projected from the lower center of the outer peripheral housing 2' of the first section 2. Thus the second flow stopping portion 3b of the second section 3 is opened by the bent elastic plate, thereby forming the separating portion.

A pressing strip 2e' for depressing an upper folding piece 8 of the second upper projection 3a of the second section 3 is projected from the upper right side of the housing 2'. In the fourth embodiment, the second outer hole 5a' is formed in the second section 3, and the first innermost hole 5c is formed in the separating projection 7.

Figure 4:
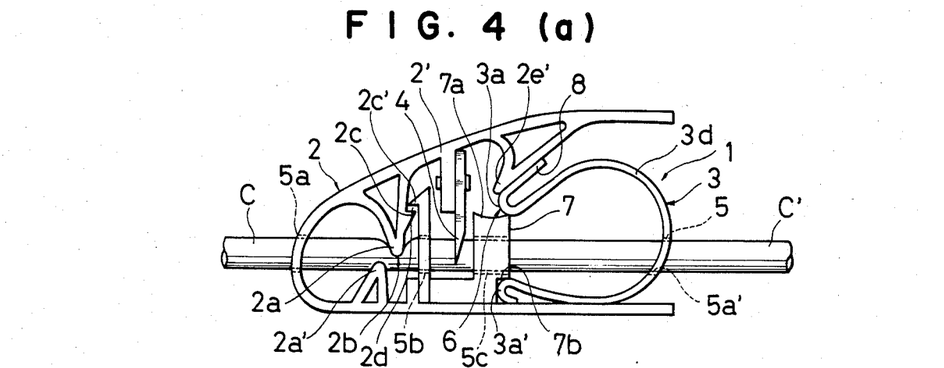
FIG. 4(a) is a front view of a fourth embodiment of the invention in the course of manual operation.
FIG 4(b) is a front view of the essential portion of the separated state of the fourth embodiment.

Therefore, in the fourth embodiment in FIG. 4, when the outer peripheral housing 2' of FIG. 4(a) is grasped in the state that the tube C is inserted into the hole 5, the pressing strip 2e' presses the upper folding piece 8 of the upper projection 3a, and thus the second upper projection 3a and the second lower projection 3a' separate from the upper end 7a and the lower end 7b of the separating projection 7.

As a result, the second section 3 is returned to the normal state as shown in FIG. 4(b) by the elastic returning force, the tube C is closed between the second upper projection 3a and the second lower projection 3a', the flow stopping state is held, and the cutter 4 provided in the same construction as in FIG. 3 cuts the tube C. Accordingly, the patient can release the second section 3 from the first section 2 remaining attached with the coupling end C'.

Figure 5:
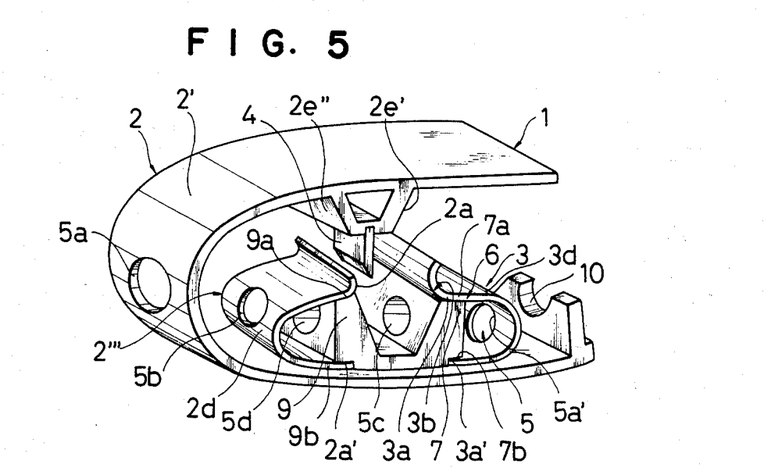
FIG. 5 is a perspective view of a fifth embodiment according to the invention.

In a fifth embodiment in FIG. 5, not only the second section 3 is formed separately by bending an elastic plate similar to FIG 4, but also the first section 2 is formed of an elastic flow stopping piece 2''' mounted detachably at the outer peripheral housing 2'.

More particularly, not only a cutter 4 is projected downward similar to the case of FIG. 4 at the upper center of the outer peripheral housing 2' of the first section 2, but also a flow stopping projection 9 substantially the same as that corresponding to the separating projection 7 described in detail with respect to FIG. 4 is projected at the left side of the cutter 4 at the lower side. First upper projection 2a and first lower projection 2a' of the elastic flow stopping piece 2''' are bent from an elastic plate art substantially the same in shape as the second section 3 and are engaged with the upper end 9a and the lower end 9b of the projection 9.

The elastic flow stopping piece 2''' is bent so that the first upper and lower projection 2a, 2a' are normally, elastically contacted with one another and when the elastic flow stopping piece 2''' is removed from the flow stopping projection 9 as will be described in detail. The bent portion of the elastic flow stopping piece 2''' performs the role of the first holding portion 2d, and the closing state of the first flow stopping portion 2b by the first upper and lower projections 2a, 2a' is accomplished by the elastic force of the bent portion.

Further, not only a pressing projection 2e' is projected similarly to the fourth embodiment of FIG. 4 at the upper side of the outer peripheral housing 2', but also a pressing projection 2e'' is projected in the opposite direction of the cutter 4. As described with respect to FIG. 4, the second section 3 is not only removed from the separating projection 7 by grasping to collapse the outer peripheral housing 2', but also the elastic flow stopping piece 2''' is removed from the projection 9 to interpose tube C between the first upper projection 2a and the first lower projection 2a' to accomplish the flow stopping state.

In the fourth embodiment in FIG. 4, a first inner hole 5b of the hole 5 is formed in the bent portion of the elastic flow stopping piece 2'''. In FIG. 5 a first intermediate inner hole 5d is formed in the projection 9, and a notched groove 10 is formed to place the tube C at the free end of the lower side of the outer peripheral housing 2'.

Figure 6:
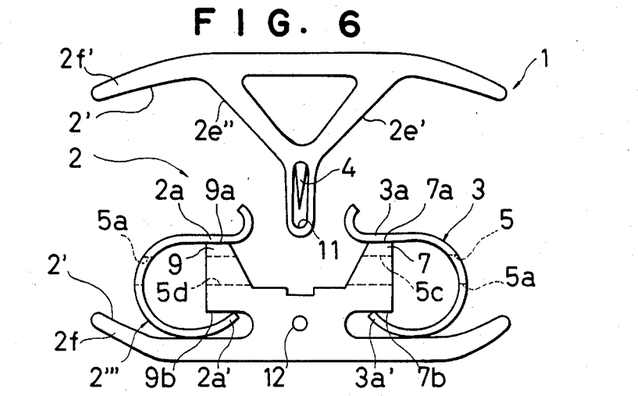
FIG. 6 is an exploded front view of a sixth embodiment according to the invention.

A sixth embodiment in FIG. 6 is substantially the same as the fifth embodiment in FIG. 5, except that the outer peripheral housing 2' of the first section 2 is formed of lower and upper housings 2f and 2f' different from the fifth embodiment that integrated U-shape. A cutter 4 and first and second pressing strips 2e'', 2e' are not only formed at the upper housing 2f' but a guide slot 11 is longitudinally formed at both front and rear sides of the cutter 4, and a shaft rod 12 projected from the front and rear wall surfaces of the lower housing 2f is inserted thereto. This shortens the separating distance of both the housings 2f and 2f' by grasping the outer peripheral housing 2' to flow stop and separate in the similar mode to that of the fifth embodiment in FIG. 5.

Figure 7A:
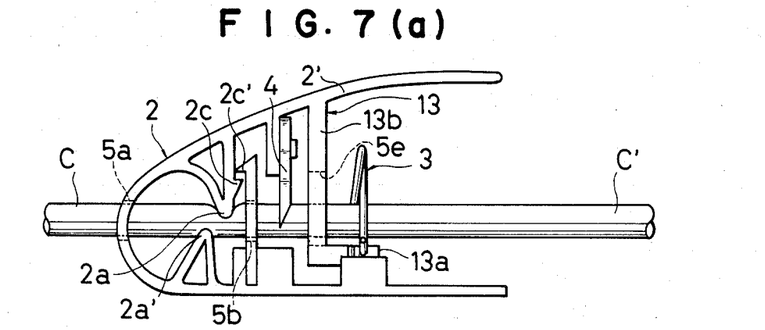
FIGS. 7(a) and 7(b) are front and perspective views of a seventh embodiment in the course of manual operation.

A seventh embodiment in FIG. 7 is substantially similar to the fourth embodiment in FIG. 4 except that both are different in the construction of second section 3 and the separating portion.

More specifically, the second section 3 is formed separately by bending an elastic strip. Thus, the second section 3 of the fourth embodiment in FIG. 4 is a C-shape, while the second section 3 of seventh embodiment is formed of an upper annular intersection 3e and a lower holder 3f substantially in a figure eight. A first flow stopping portion 2b capable of stopping the flow through the interposed tube C is formed between the first left side projection 2a'' and the first right side projection 2a''' *forming the lower holder 3f.* The upper annular intersection 3e of an elastic source forms a first holding portion 2d for holding the flow stopping state.

Figure 7B:
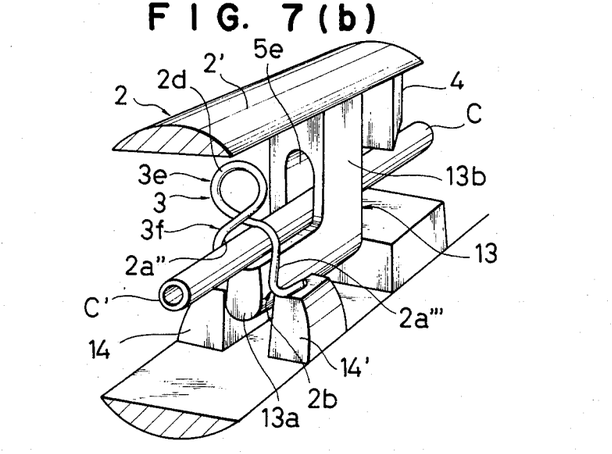

In order to then form a separating portion, an L-shaped separating removing rod 13a, b is projected from the upper side of the outer peripheral housing 2'. A lateral portion 13a of the lower end side is resisted against the elastic force of the lower holder 3f of the second section 3 and is interposed between the first left side projection 2a'' and the first right side projection 2a'''. In this case the both lower ends of the lower holder 3f are placed on placing projections 14, 14' projected from the lower end side of the outer peripheral housing 2' as shown in FIG. 7(b). In this case the longitudinal portion 13b of the separating removing rod 13a, b is projected longitudinally including a first innermost side hole 5e of the hole 5.

Therefore, when the housing 2' is grasped to be collapsed similarly to the other embodiments, the rod 13a, b between the projections 14 and 14''' is removed from the lower holder 3f. Thus, the tube C is interposed between the first left side and the first right side projections 2a'' and 2a''' to hold the flow stopping state. Thus, in the seventh embodiment in FIG. 7, the separating portion is formed of the second section 3 and the rod 13a, b detachably attached thereto in contact with one another.

Figure 8:
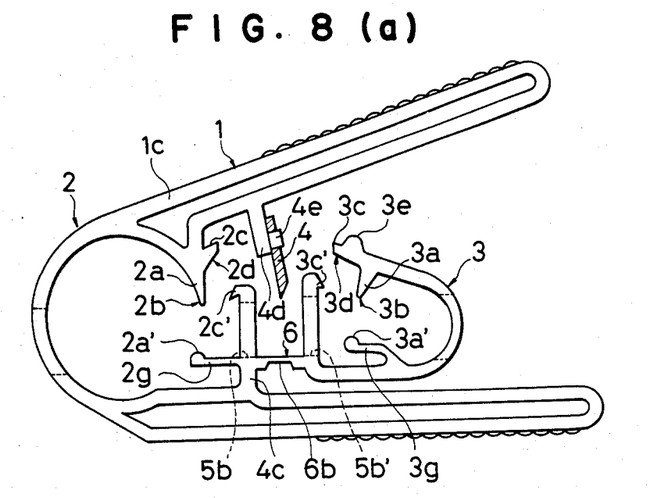
FIGS. 8(a) and 8(b) are front views of an eighth embodiment before manual operation and immediately after the manual operation.

In an eighth embodiment in FIG. 8, first flow stopping portion 2b of a first section 2 and a second flow stopping portion 3b of a second section 3 are different from the other embodiments.

More particularly, the first and second upper projections 2a, 3a of the first and second sections 2, 3 are similar to the above embodiments. First and second lower projections 2a', 3a' are, when pressed, bendable by extending first and second elastic arms 2a, 3g.

Therefore, according to this construction of the eighth embodiment in FIG. 8, when the thickness of the tube C is relatively thin, the tube C and the separating thin film 6b of the separating portion 6 can be not only effectively cut and separated by the cutter 4 as described above. Even if the thickness of the tube C is large, when the tube C is pressed by the first and second upper projections 2a, 3a, the first and second elastic arms 2g, 3g of the first and second lower projections 2a', 3a' are bendable downwardly. Thus, the first and second flow stopping portions 2b, 3b stop flow, and the first and second holding portions 2d, 3d can effectively hold to complete the cutting operation by the cutter 4.

Figure 9A:
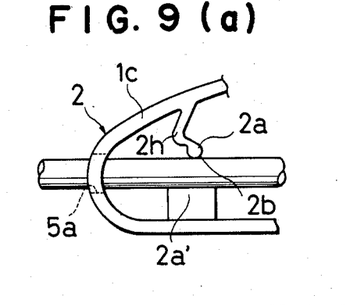
FIGS. 9(a) and 9(b) are front views of a ninth embodiment before manual operation and manual operating time.
Figure 9B:
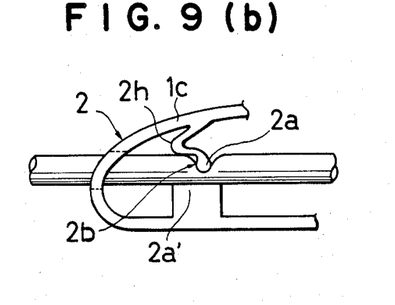

In a ninth embodiment in FIG. 9, the first lower projection 2a' is formed oppositely to the construction of the first and second flow stopping portions 2b, 3b is the eighth embodiment in FIG. 8. The first upper projection 2a is formed to be transformable as in FIG. 9(b) from the elongated state of FIG. 9(a).

In other words, a bendable elastic portion 2h is bent of the intermediate position at the first upper projection 2a, and when a tube C of larger diameter is used as described above, the portion 2h is bent to be contracted.

In the eighth embodiment in FIG. 8, the first and second sections 2, 3 are integrally formed, but in use, by grasping the first section 2, the second section 3 is pressed by the first section 2. And reference numeral 3e designates a pressing bearing strip projected at the second section 3 for pressing the first section 2.

The fastening means of the cutter 4 is formed by a projection 4e projected from a mounting arm 4d connected to the outer peripheral frame 1c. The cutter 4, and the projection 4e are thermally calked. Numerals 1d, 1d''' designate antiskid portions formed at the grasping position of the frame 1c.

In the embodiments described above, one side of the first and second upper projections 2a, 3a and the first and second lower projections 2a', 3a' are elastically transformable by a spring action. However, both sides may be formed to be all elastically transformable in a spring action.

According to the embodiments described above by, even though the thickness of the tubes C may be irregular, flow in the tube may be sufficiently stopped. Therefore, one cutting and separating implement can be used universally for various conduits. Even if used for a constant size conduit, in case of manufacturing the cutting and separating implement of the invention, the range of the dimensional contraction at molding time can be increased during production, and the molds do not require severe dimensional accuracy.

Since the invention is constructed as described above, the patient or worker can very simply manually operate by merely grasping the implement on the tube, thereby rapidly storing the flow in the tube and cutting the tube by the cutting and separating implement of the invention. As a result, the patient can be released without discharging blood or medicine without the assistance of a nurse or other person in an emergency situation.

Since the implement of this invetion can be readily molded of synthetic resin, it can be color coded for identification.

What is claimed is:

1. A tube cutting and separating implement for a conduit containing a flowing fluid comprising:

a housing, said housing having separable portions, an elongated base having a longitudinal axis and clamping means connected for movement relative to said base;

means in said housing for receiving a tube aligned substantially parallel to the longitudinal axis of said base;

means in said housing for maintaining said tube closed in each of said housing portions; and severing means carried by one of said portions for severing said tube between said portions, whereby upon one-handed movement of said clamping means along a plane parallel to the longitudinal axis of said base, said tube is severed, said severed ends of said tube are maintained closed in each of said portions and said portions are separated.

2. The implement of claim 1 wherein said clamping means includes a pair of members pivotally movable relative to said base.

3. The implement of claim 2 wherein said portions are separated by a break tab.

4. The implement of claim 3 wherein said break tab is severed by said severing means.

5. The implement of claim 1 wherein said clamping means includes a single member pivotally movable relative to said base.

6. The implement of claim 5 wherein said housing carries a resilient member and said resilient member is actuated into a tube clamping position in response to movment of said clamping means towards said base.

7. The implement of claim 6 wherein said resilient member is separable from said housing.

8. The implement of claim 1 wherein said clamping means simultaneously severs, closes and separates said separable portions upon said one-handed movement.

9. The implement of claim 1, wherein said housing is substantially U-shaped and includes a C-shaped separable portion urged to a normally closed clamping position in response to said one-handed movment.

10. The implement of claim 1, wherein the housing is formed of an elastic flow stopping piece and a separable portion is formed separately by bending an elastic plate.

11. The implement of claim 1, wherein a separable portion is formed separately by bending an elastic strip shaped as a figure eight and is urged to a normally closed clamping position in response to said one-handed movement.

12. The implement of claim 1, wherein the separable portions include first and second elastic arms, respectively, said second elastic arm being urged to a clamping position by said first elastic arm in response to said one-handed movement.

* * * * *